United States Patent [19]
Gargano et al.

[11] Patent Number: 5,629,678
[45] Date of Patent: May 13, 1997

[54] PERSONAL TRACKING AND RECOVERY SYSTEM

[75] Inventors: Paul A. Gargano, 154 Clifton St., Belmont, Mass. 02178; David H. Gilmore, Cayman Kai, Cayman Islands; Frank A. Pace, Ballston Spa, N.Y.; Lee Weinstein, Somerville, Mass.

[73] Assignee: Paul A. Gargano, Belmont, Mass.

[21] Appl. No.: 371,089

[22] Filed: Jan. 10, 1995

[51] Int. Cl.⁶ .................................................. G08B 23/00
[52] U.S. Cl. ........................ 340/573; 128/903; 340/539; 340/825.49; 342/357; 455/100
[58] Field of Search ........................ 340/573, 574, 340/572, 539, 825.49; 455/100; 379/37–38; 342/450, 357, 44, 42, 51; 128/774, 903, 653.1, 696

[56] References Cited

U.S. PATENT DOCUMENTS

| | | | |
|---|---|---|---|
| 3,618,059 | 11/1971 | Allen | 340/572 X |
| 3,815,611 | 6/1974 | Denniston, III | 607/17 X |
| 4,453,537 | 6/1984 | Spitzer | 623/3 |
| 4,594,997 | 6/1986 | Hakky | 600/40 |
| 4,602,621 | 7/1986 | Hakky | 600/40 |
| 4,706,689 | 11/1987 | Man | 340/539 X |
| 4,713,054 | 12/1987 | Kelly et al. | 604/89 |
| 5,007,927 | 4/1991 | Badylak et al. | 623/3 |
| 5,051,741 | 9/1991 | Wesby | 340/825.49 |
| 5,318,501 | 6/1994 | Lee et al. | 600/16 |
| 5,342,408 | 8/1994 | de Coriolis et al. | 607/32 |
| 5,456,715 | 10/1995 | Liotta | 623/3 |
| 5,461,365 | 10/1995 | Schlager et al. | 340/573 |
| 5,461,390 | 10/1995 | Hoshen | 340/573 X |
| 5,476,488 | 12/1995 | Morgan et al. | 128/903 X |

OTHER PUBLICATIONS

Dialog OneSearch Results, May 13, 1994.

*Primary Examiner*—Thomas Mullen
*Attorney, Agent, or Firm*—Hamilton, Brook, Smith & Reynolds, P.C.

[57] ABSTRACT

Apparatus for tracking and recovering humans utilizes an implantable transceiver incorporating a power supply and actuation system allowing the unit to remain implanted and functional for years without maintenance. The implanted transmitter may be remotely actuated, or actuated by the implantee. Power for the remote-activated receiver is generated electromechanically through the movement of body muscle. The device is small enough to be implanted in a child, facilitating use as a safeguard against kidnapping, and has a transmission range which also makes it suitable for wilderness sporting activities. A novel biological monitoring feature allows the device to be used to facilitate prompt medical dispatch in the event of heart attack or similar medical emergency. A novel sensation-feedback feature allows the implantee to control and actuate the device with certainty.

19 Claims, 2 Drawing Sheets

PERSONAL TRACKING AND RECOVERY SYSTEM

BACKGROUND OF THE INVENTION

The present invention relates, in general, to tracking and recovery systems and systems for tracking and recovering humans. More particularly, it discloses a system employing a self-powered, self-maintained transceiver, small enough to be implanted in a human, for locating, tracking, and recovering persons in distress, such as kidnap victims, people encountering adverse circumstances while in the wilderness, victims of heart attacks and the like.

BACKGROUND OF THE INVENTION

Various apparatus and techniques for tracking and locating animate and inanimate objects are known in the art. Recently, international legislation has established a satellite tracking system for locating downed aircraft and distressed seagoing vessels. This system utilizes user-activated transmitters operating at a frequency of 460 MHz, as spelled out in the Code of Federal Regulations chapter 47 part 90. These inexpensive transmitters are known as Emergency Position Indicating Radio Beacons (EPIRB's). The associated satellite network is capable of locating a transmitting EPIRB anywhere on the face of the globe. By international agreement, this system is used only for distressed aircraft and seagoing vessels, and all other potential uses are forbidden.

U.S. Pat. No. 4,818,998 describes a vehicle tracking and recovery system employing a transceiver (to be hidden within a motor vehicle), and a network of fixed and mobile ground transmitters and receivers to facilitate tracing and recovery of stolen vehicles. This system is presently in wide use by LoJack Corporation in the United States. The system operates at a frequency of 173.075 MHz, permanently assigned as a police radio service frequency in 1992. The unit, mounted in an automobile, is continuously operated as a receiver until such time as it is remotely activated, at which time it transmits a radio beacon (similarly to the EPIRB system), facilitating tracking and recovery. The tracking and recovery in the LoJack system is accomplished through a network of ground based fixed and mobile receiver units, which utilize field strength measurements and directional receivers to locate the transmitter, as opposed to the timing and triangulation methods used by the EPIRB system. The receiver in the automobile-mounted unit draws its power from the vehicle battery, and utilizes a small local rechargeable battery that powers the unit should the vehicle battery be disconnected.

U.S. Pat. No. 4,706,689, Issued to Daniel Man on Nov. 17th, 1987, describes a device designed to be implantable behind the ear of a human. The device transmits a coded signal intended to enable tracking of the person outfitted with the implanted device. The device operates continuously, and is designed to be recharged through external contacts. It is also designed to incorporate a biological monitoring function, such as might facilitate out-patient monitoring.

The above described devices all have limitations making them unsuitable as systems for the widespread tracking and recovery of humans. The EPIRB transmitter and Lojack transceiver are not miniaturized to the point where implantation is practical. The techniques for manually activating the EPIRB unit also make it unsuited for implantation. The LoJack unit requires substantial power to be supplied continually from a vehicle battery system, and unsuited for implantation from this point of view as well.

Daniel Man's implantable device is designed for continuous operation, which places severe constraints on its transmission range, even if it is only to be operated for a day at a time between battery recharges. With a given level of background radio frequency noise, communication theory can be used to calculate the minimum power consumption needed for detection of an event within a given time to within a given certainty, at a given distance from an omnidirectional transmitter. The resultant average transmission power is independent of whether the transmitter is pulsed or continuous. Further problems arise with Man's system when a number of units are in use in the same area. The tracking problem becomes prohibitively expensive for many simultaneous units, and the malfunction of any unit can mask the detectability of other units, or require significantly increased transmission power levels for all units. Such a system would require a very expensive closely spaced network of permanent tracking receivers with very costly hardware capable of tracking multiple units at one time. A system where transmitters are active all the time requires n times more bandwidth in the radio spectrum than minimal-bandwidth system with only one transmitter transmitting at one time. The availability of bandwidth could become quite a problem if the Man system were put into wide use.

In addition, the implanted unit would need to be recharged (probably daily) through contacts brought out through the person's skin. Such an arrangement presents a significant health hazard. In addition, the need for regular recharging puts significant restraints on the person using the device and also heightens the users awareness of the implanted device, resulting in a less "free and natural" state of mind. The complexity of the Man system could result in a significant level of false alarms, and/or prohibitively high cost.

The present invention contemplates improving upon the features available in the aforementioned devices and makes possible a widespread tracking and recovery system for humans in distress. The present invention will benefit from novel features allowing it to remain implanted and functional for many years. The device will remain in a dormant state until activated, either by the person in whom it is implanted, or by remote means. Novel means for powering and triggering the device will make recharging and battery replacement unnecessary. The device meets the growing demand for a new level of safety and peace of mind.

Consequently, it is a general object of this invention to provide a new means and method for locating, tracking, and recovering humans in distress. Ideally, the device will bring peace of mind and an increased quality of life for those who use it, and for their families, loved ones, and associates who depend on them critically. Adults who are at risk due to their economic or political status, as well as their children who may be at risk of being kidnapped, will reap new freedoms in their every-day lives by employing the device. Law enforcement agencies will be able to more economically protect those at risk, those who would potentially perpetrate acts of violence against individuals will be more effectively deterred. Those who enjoy wilderness sports such as mountain climbing, skiing, hang gliding, etc. will enjoy new freedom knowing that a rescue mission can be dispatched to their exact location if they encounter trouble.

A specific object of the invention is the rapid effective recovery of individuals who have been kidnapped. A further object of this invention is to afford peace of mind and increased quality of life to those utilizing the invention, and to their loved ones and dependent associates. It is a further object of the invention to make emergency aid readily available to those at risk in remote or urban areas. It is a further object of the invention to reduce the cost of rescue missions to remote areas. It is further object of the invention to facilitate a highly reliable, minimal cost, location and recovery system with flexible features. It is a further object of the invention to facilitate rapid, automatic deployment of medical personnel in the event of certain medical emergencies.

This implantable tracking and recovery device makes possible greatly increased safety for people in a variety of situations. This increased safety leads to peace of mind and associated increased quality of life not only for those utilizing the device but for concerned loved ones as well. Four areas where this device will be seen to have significant impacts are (1) safeguarding against kidnapping, and rapid recovery of victims; (2) safety in wilderness sporting activities, where risk is inherent and help is often not readily available; (3) personal safety in urban environments, where one might encounter car-jackings, muggings, and the like; (4) medical emergencies, such as heart attack or seizure.

The lives of potential kidnap victims and their loved ones will be significantly freed up by the peace of mind afforded by the tracking device. Along with peace of mind, the homing device will offer the possibility of a lifestyle that would otherwise be considered too risky. In the event of a kidnapping, law enforcement officials could be expediently dispatched for rapid recovery of the victim.

The tracking device will offer safety in such activities as hiking, mountain climbing, skiing, and camping in remote areas. Costs of rescue missions will be dramatically cut because searching will not be necessary. Lives will be saved because the time from when the emergency occurs to when help arrives will be dramatically cut.

The device will afford increased safety and peace of mind for those in urban areas as well. The increase in gang violence, rapes, muggings, and car jackings in recent years has generated significant increased concern for personal safety. The use of the device will afford increased peace of mind and will allow law enforcement to be more effective.

Many lives could be significantly prolonged if help were rapidly available in the event of a heart attack. Unfortunately, the individual suffering the heart attack may not recognize the symptoms of the heart attack (which may occur in sleep), and even if the symptoms are recognized, the individual may be unable to summon help. The use of the device with incorporated body-function monitoring capability allows help to be rapidly dispatched, potentially saving the life of the user.

SUMMARY OF THE INVENTION

The system employs triggerable radio beacon transmitter means designed to be implanted beneath the skin of an individual. Biological monitoring in the device will provide means for rapidly dispatching help in the event of a detectable medical emergency, such as a heart attack. A unique sensation-feedback feature allows the user to control and trigger the device with certainty, resulting in a more reliable, easily maintained system. The device is hermetically sealed in a biologically inert container. The device operates normally in a dormant state, and can be externally triggered to transmit the homing beacon. There are numerous possible embodiments of the trigger mechanism. In some embodiments of the trigger mechanism, the device is designed to be remotely triggered. Such a feature is desirable if the device is implanted in a small child who cannot be relied upon to trigger the device. Remote triggering may also be desirable in instances when an individual may be unconscious.

In one remote triggering instance, a radio transmitter may broadcast a coded signal to a receiver within the device. The receiver is equipped with circuitry for recognizing the coded radio signal. In one embodiment where the device is locally triggered, the device may be equipped with an acoustic receiver designed to detect certain sounds or a predetermined sequence of sounds in time, such as a note progression. In this case the device would likely be triggered by the person in whom it is implanted, for instance by humming a given tune. Immunity to false alarms may be provided by making the sequence long or requiring it to be repeated in a certain amount of time.

In another embodiment, the device may be triggered by monitoring a body function such as heart rate. If the victim were to experience a heart attack, help would be automatically and expediently dispatched.

If the device is triggered either by an external coded radio signal or a coded acoustic signal, or by monitoring a body function such as heart rate, the device incorporates a micro-power analog electronic means such as a radio or acoustic receiver or electrocardiogram monitoring circuitry, which runs off energy collected either from body muscle by electromechanical means, or from an external charger through electromagnetic induction coupling.

Other local triggering means not requiring a micro-power receiver are also contemplated. In such a case the device may be triggered by electromechanical means with a binary output, such as a mechanical switch. Possible embodiments of such a triggering mechanism range from a simple subcutaneous switch or combination of switches that actuate the transmitter when pressed, to an actuator coupled to internal body muscle, combined with digital circuitry designed to trigger the transmitter in response to a timed sequence of actuations.

It may be desirable in some implementations to include capabilities for both local and remote triggering. The same individual may desire the capability of local triggering in the event of an emergency such as a car-jacking, mugging, or kidnapping, while desiring remote triggering capability if for some reason the situation had rendered the individual unconscious. It may also be desirable in some embodiments for the user to be able to disable the remote-trigger feature.

The device contains a power source capable of supplying power for the transmitter for ample time to afford recovery of the individual in distress. Once triggered, the device may transmit only for a predetermined interval, allowing re-triggering later if the distressed individual is not located, or if help takes some time to dispatch.

The small size of the device makes it suitable for implantation in young children as well as adults. The above and other features of the invention including various and novel details of construction and combination of parts will now be more particularly described with reference to the accompanying drawings and pointed out in the claims. It will be understood that the particular personal tracking and recovery system embodying the invention is shown by way of illustration only and not as a limitation of the invention. The principles and features of this invention may be employed in varied and numerous embodiments without departing from the scope of the invention.

DETAILED DESCRIPTION OF THE INVENTION

Figure 1:
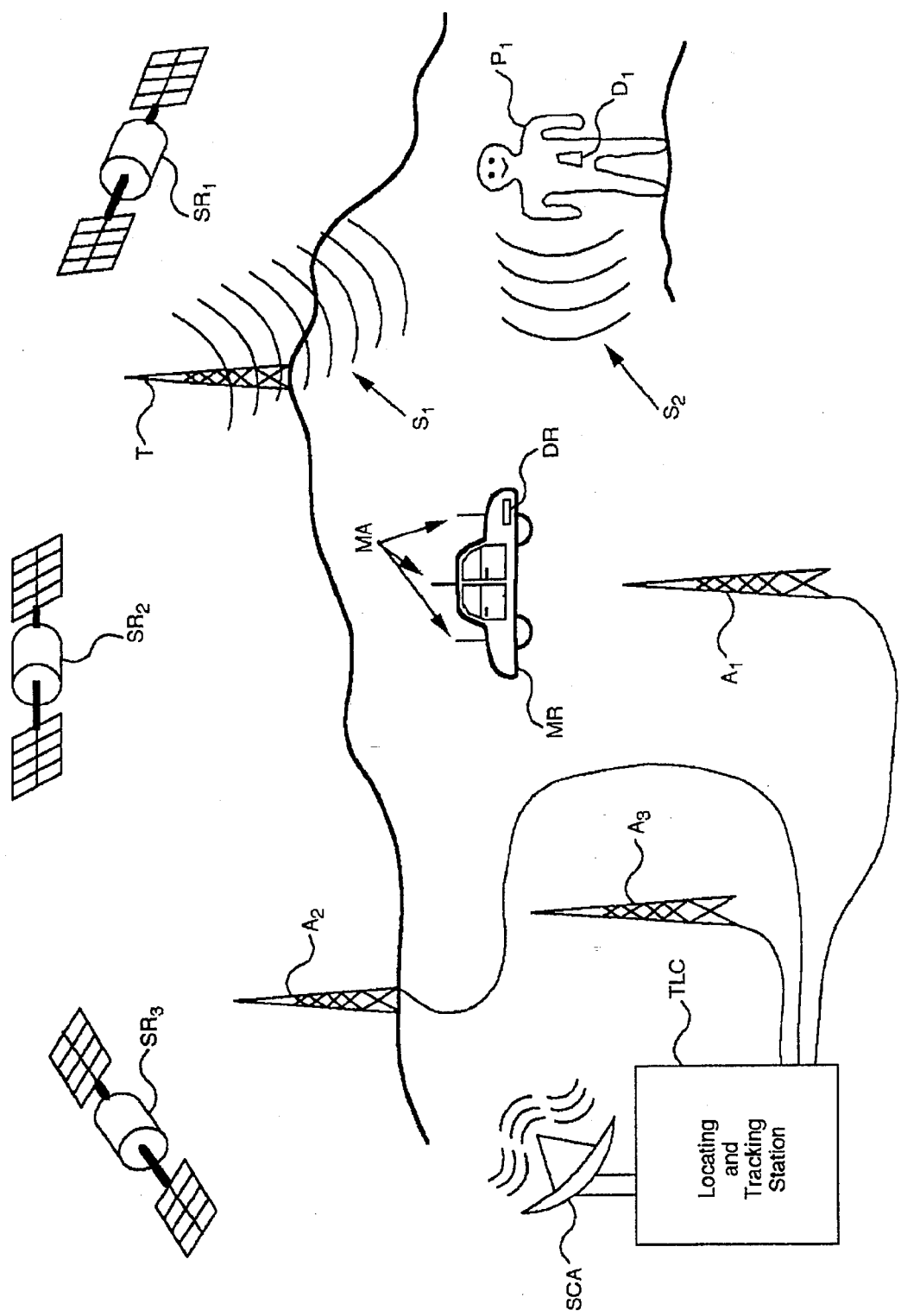
FIG. 1 depicts an overall schematic view of a system for the tracking, locating, and recovery of humans embodying the features of the invention and including an exemplary implantable triggerable transmitting device, remote activation transmitter, several ground-based receiving antennae and alternate satellite-based receiving antennae, mobile receiving unit, and associated coordinating equipment, which combine to perform the locating and tracking function.

Referring to FIG. 1, one of a plurality of persons, $P_1$, is equipped with an implanted transceiver device $D_1$ from a plurality of devices D. A plurality of triggerable transmitters T (only one of which is shown in FIG. 1) transmit a coded trigger signal $S_1$, which is picked up by the receiver section of all implanted devices D (only device $D_1$ being shown in FIG. 1). The receiver circuits in all devices D receive the same coded trigger signal. However, the code in signal $S_1$ uniquely identifies device $D_1$, and $D_1$ alone responds to coded signal $S_1$ by transmitting a locating-and-tracking signal $S_2$. Signal $S_2$ is received by at least one ground-based receiver, $A_1$, $A_2$, and $A_3$, of a plurality of receivers A, or at least one satellite receiver including $SR_1$, $SR_2$, and $SR_3$ of a plurality of receivers R.

Information from the ground-based receivers A or the satellite receivers S are coordinated at a tracking and locating center TLC. Equipment within the tracking and locating center TLC uses information (for example phase, timing, field strength, etc.) of the received signals to derive positional information about implanted device $D_1$. Additional positional information may be provided by a mobile receiver MR, which may employ directional receiving means DR, and one or more antenna MA. The mobile receiver MR may be used, for instance, to locate implantable unit $D_1$ within a building, a neighborhood, or a small area of wilderness, facilitating cost effective recovery without having to map the face of the globe precisely.

Upon being triggered by signal $S_1$, implanted device $D_1$ preferably transmits only for a brief interval long enough to get a rough positional fix. When the mobile receiver MR has been dispatched, or other rescue means have been readied, transmitter T would then re-activate implanted device $D_1$ for the second stage of the recovery.

Figure 2:
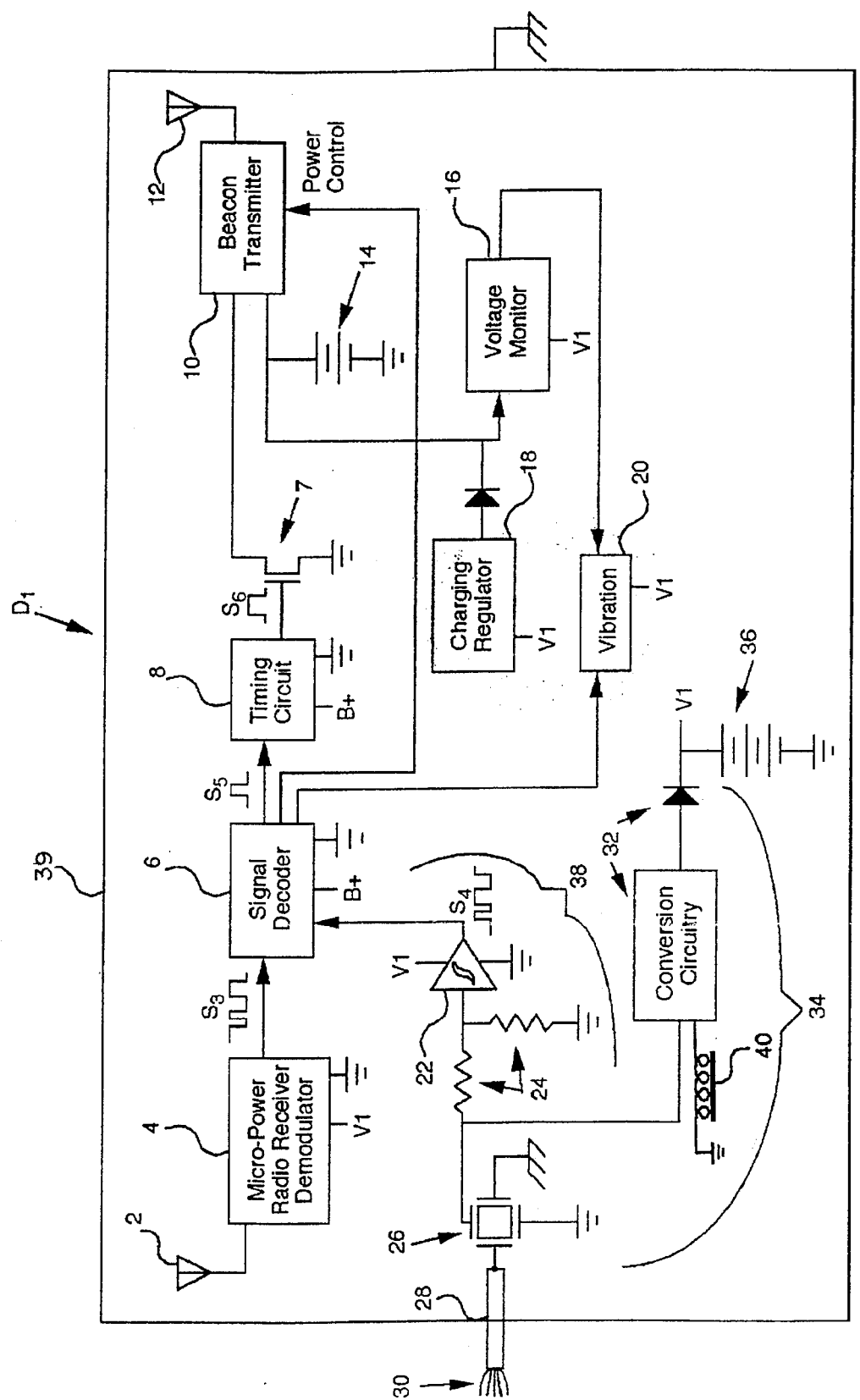
FIG. 2 is a schematic block diagram of an illustrative implantable triggerable transmitter unit, including sensation feedback feature, and several trigger implementations, which are used separately or in combination in a given embodiment of the implantable device.

FIG. 2 is a mechanical and electrical schematic block diagram of an exemplary implantable triggerable transceiver unit $D_1$. The entire unit $D_1$ is housed within a sealed case and designated 39. The case is preferably made from or covered with a biologically inert material such as Teflon or Titanium. Several possible mechanisms are shown. Remote radio receiving means comprise a receiving antenna 2 and micro-power radio receiver/demodulator means 4. The triggering signal $S_1$ is received by antenna 2, and the resultant electrical signal is fed to the micro-power radio receiver/demodulator means 4, which outputs a binary signal $S_3$ to signal decoder means 6. The signal decoder means 6 monitors signal $S_3$ over time, and upon detecting a certain pre-determined pattern, sends a trigger signal $S_5$ to timing circuit means 8. Timing circuit means 8 then applies a control signal $S_6$ to a power switching means 7, causing power switching means 7 to apply power from power source 14 to a beacon transmitter 10, which may broadcast at different power levels, controlled by signal decoder means 6.

The beacon transmitter 10 operates in response to being actuated by power source 14, and transmits the locating and tracking signal $S_2$ via transmitting antenna 12. Through the incorporation of proper input protection circuitry on the micro-power receiver 4, it is possible for receiving antenna 2 and transmitting antenna 12 to be one and the same. These antennae are shown as being separate in FIG. 2 for functional clarity. The micro-power receiver means 4 is powered by energy storage means 36. Micro-power generating means 26 may derive power from some energy source external to the implanted device.

In the preferred embodiment, micro-power generating means 26 derives power from physical work done by muscle fibers in the body. Body muscle 30 is connected (for instance, via suturing) to linkage 28. Linkage 28 connects muscle 30 through a seal in case 39 to micro-power transducing means 26. Case 39 is mechanically anchored to another body structure (for instance muscle, tendon, bone, etc.) to afford an opposing force to that exerted by muscle 30. Power transducing means 26 converts the work of muscle 30 to useful electrical energy, which is fed to energy conversion circuitry 32. Energy conversion circuitry 32 is provided to most efficiently store the electrical energy derived from power transducing means 26 in energy storage means 36. Energy storage means 36 serves as an energy reservoir for micro-power circuitry 34. Micro-power receiver 4 may be implemented similarly to receiver sections used in miniature commercial pagers. Power transducing means 26 may be a piezoelectric device (the preferred embodiment), electromagnetic induction device (such as a moving magnet generator), or the like. Linkage 28 is preferably sealed to case 40 with a flexible membrane.

Energy storage means 36 holds enough energy to sustain micro-power circuitry in an operational state with enough regularity to insure proper triggering of beacon transmitter 10 in response to trigger signal $S_1$. The duty cycle requirements of the availability of power from energy storage means 36 may be traded off against the length of time the activation signal $S_1$ is sent out. In the preferred embodiment, there is enough power available from energy reservoir 36 to power micro-power receiver/demodulator means 4 100% of the time.

Power-switching means 7 is shown as a field-effect transistor, chosen in the preferred embodiment because it takes no static power to keep turned on, yielding easy interface with micro-power circuitry, and also allowing a high degree of integration onto a single chip. Signal decoding circuitry 6 and timing circuitry 8 are preferably CMOS logic, in order to draw minimal power. Timing circuitry 8 is preferably powered from power source 14, in order that brief lapses in the availability of power from energy storage reservoir 36 will not affect the timing of beacon transmitter 10.

Signal decoder means 6 may be made capable of detecting multiple codes to perform different functions, for instance to activate beacon transmitter means 10 for different periods of time. A short-time actuation might be desirable for an initial positional fix, and a long-time actuation might be desirable for a final local recovery by a mobile receiver. It is desirable to have different activation codes result in beacon transmitter 10 being energized at different power levels, for instance a high power level for the initial positional fix, where the receiving antennae may be far away, and a lower power level during the final positional determination by a mobile receiver.

Binary conversion means 38 converts the analog signal derived from power transducing means 26 to a digital signal.

In the preferred embodiment, this enables body muscle 30 to be used to control the implanted device as well as provide power to the device. Contractions of body muscle 30 cause alternating voltage signal $S_5$ to be generated and applied to energy conversion circuitry 32 and binary conversion means 38. For the piezoelectric power transducing means of the preferred embodiment, binary conversion means 38 may be implemented as a voltage divider means 24 followed by Schmitt trigger means 22. Binary conversion means 38 is powered by energy storage reservoir 36, in order to avoid draining the standby power source 14. The output of binary conversion means 38 feeds an input on signal decoder means 6 with a digital signal, allowing signal decoder means 6 to be entirely digital CMOS circuitry such as common in wristwatches, which can be made to draw so little power that the drain on power source 14 would be inconsequential, even over a number of years.

Signal decoder 6 may provide different decoding functions for data streams from different sources. For instance, signal $S_4$, derived locally, may be decoded to provide functions not accessible remotely, such as shutting down micro-power receiving means 4. This may be desirable if the user is worried about being locatable by an adverse party under certain circumstances. Partial completion of the trigger code in data stream $S_4$ may be programmed to provide a perceivable sensation to the user, for instance through vibrator means 20. This would provide means for "practicing" triggering the device without actually sending out a signal indicating an emergency. It is also possible to configure the device to provide the same or different perceivable sensation through vibrator means 20 upon activation of Beacon transmitter 10. This feedback would provide peace of mind to the user, knowing that help was on the way. Various self-test functions may be implemented through special codes recognized in signal stream $S_4$.

Voltage monitor means 16 is provided to detect a low-energy state of power source 14. Voltage monitor means 16 is preferentially powered off energy reservoir 36, ensuring that the critical standby power source 16 is not drained by providing the voltage monitoring function. Voltage monitor means 16 may also activate vibrator means 20 in such a way as to provide a sensation uniquely indicating low power.

It is contemplated that in one embodiment, energy reservoir 36 and power source 14 would be one and the same. This has not been done in the preferred embodiment for three reasons: First, the most suitable embodiment of power source 14 is deemed to be a chemical storage battery with a long (perhaps 10 year) expected shelf life. This ensures that adequate power for beacon transmitter 10 is available reliably, while taking very little space. Second, regular "playing" with vibrator means 20 could, in such an instance, result in substantially draining power source 14 for some period of time. Third, implementing energy reservoir 36 with a different type of energy storage device than 14 (for instance, implementing 36 as a capacitor) can allow for increased charging efficiency over the relatively low electrochemical charging efficiency of many batteries.

For very long term applications or to reduce the shelf life requirements on power source 14, voltage regulator means 18 may be provided to use surplus energy collected from power transducing means 26 to keep power source 14 optimally charged.

It may be desirable to separate the receiving and/or transmitting antennae 2 and 12 from the rest of the unit, in order to allow the antennae to be closer to the surface of the body for more efficient transmission and reception. Such mechanical alterations to the containment of the device are within the scope of the present invention.

It is also possible for the conversion circuitry 32 to receive power from a source external to the body, such as an electromagnetic induction source that might be placed close to the body on a regular basis for purposes of recharging energy reservoir 36. In such an embodiment inductive pickup means 40 receives electromagnetic energy from a source external to the body. Such implementation is considered less desirable because it affords the user less personal freedom, and results in a system which is less robust overall.

The drawings referred to in the specification are presented in block diagram form. Numerous possible implementations of any given block will be apparent to one skilled in the art. Any specific details referred to are strictly by way of example. It will be readily apparent to one skilled in the art that various substitutions and modifications can be made without departing from the spirit of the invention.

We claim:

1. A transceiver device implantable in a human body comprising:
    a triggerable radio frequency transmitter,
        a power source for powering said transmitter,
        triggering means for activating said transmitter,
        receiver means allowing the detection of an externally generated information signal,
        an antenna for effectively radiating RF energy from said transmitter to produce an identifiable RF signal for a period of time following activation by said trigger means,
        said receiver means comprising an electromechanical device having a binary output, a digital decoder for detecting predetermined time-encoded information in the binary output of said electromechanical device and for providing an electrical trigger signal representative of the presence of such pre-determined information, and
        said trigger signal causing the activation of said transmitter.

2. The transceiver of claim 1, wherein said receiver means additionally comprises a wave receiver for receiving a transmitted wave, and
    said digital decoder is responsive to information in an incoming transmitted wave for providing an electrical trigger signal representative of the presence of the information.

3. The transceiver of claim 2, further comprising sensory stimulus means for providing a noticeable stimulus to alert the person in whom the device is implanted that all or part of said incoming transmitted wave has been detected by said digital decoder.

4. The transceiver of claim 2, further comprising a charging regulator for maintaining the power source used to power the transmitter at a state of peak charge.

5. The implantable device of claim 1, wherein said receiver means additionally comprises a sustainable power supply comprising means for picking up periodically available external energy without external electrical contact, storing said energy for use over time, such that the resultant stored energy is sufficient to power the receiver means with enough regularity to ensure proper detection of information on said incoming signal.

6. The transceiver of claim 5 wherein said external energy pickup comprises an inductive pickup, for converting magnetic energy to electrical energy.

7. The transceiver of claim 6, wherein said inductive pickup is placed close to the surface of the body of the individual in which it is implanted.

8. The transceiver of claim 5 wherein said external energy pickup comprises an electromechanical means for converting mechanical work of the body into electrical energy.

9. The transceiver of claim 8, wherein said mechanical work is supplied by muscle tissue in the body of the human in which the device is implanted.

10. The device of claim 1, wherein said electromechanical device includes threshold-detection circuitry.

11. The device of claim 1, wherein said signal decoder allows input from more than one source of binary information.

12. The device of claim 1, further comprising means for providing a perceivable stimulus in response to one output from said digital decoder.

13. The transceiver of claim 12, wherein said receiver means comprises analog circuitry for amplifying the electrical field associated with the contraction of the human heart, and said digital decoder comprises means for detecting the lack of a regular heartbeat.

14. The device of claim 1, wherein said signal decoder provides a plurality of outputs in response to a plurality of different pre-determined information patterns.

15. The transceiver of claim 1, further comprising sensory stimulus means for providing a noticeable stimulus to alert the human in whom the device is implanted that all or part of said externally generated information signal has been detected by said digital decoder.

16. The transceiver of claim 1, further comprising sensory stimulus means for providing a noticeable stimulus to alert the human in whom the device is implanted that the all or part of said predetermined information signal has been detected by said detector means.

17. The device of claim 1, wherein said digital decoder allows input from more than one source of binary information.

18. A system for tracking and recovering humans in distress, comprising;

a plurality of triggerable transceivers implanted each in a human being, each transceiver having a transmitter and a receiver, any one of said transmitters of said transceivers uniquely triggerable to transmit a radio frequency beacon signal after the receiver of said transceiver receives a predetermined radio frequency information signal, a network of trigger transmitters and receivers, each being sensitive to said radio frequency beacon signal and capable of deriving positional information concerning the source of said beacon signal, and said trigger transmitters being capable of transmitting a plurality of uniquely identifiable radio frequency information signals, capable of uniquely triggering one of the plurality of implanted radio transceivers.

19. The system of claim 18, further comprising a plurality of mobile receivers sensitive to said radio frequency beacon signals for providing finer positional accuracy in determining the location of the source of said radio frequency beacon signals.

* * * * *